United States Patent [19]

Stewart et al.

[11] Patent Number: 4,869,497
[45] Date of Patent: Sep. 26, 1989

[54] COMPUTER CONTROLLED EXERCISE MACHINE

[75] Inventors: Gary D. Stewart, Scottsdale; Todd M. Johnson, Mesa; Patricia B. Orman, Paradise Valley; Joseph W. Lambright, Phoenix; Gary M. Orman, Paradise Valley; Rodney E. Schwartz, Tempe, all of Ariz.

[73] Assignee: Universal Gym Equipment, Inc., Cedar Rapids, Iowa

[21] Appl. No.: 5,035

[22] Filed: Jan. 20, 1987

[51] Int. Cl.$^4$ .............................................. A63B 23/00
[52] U.S. Cl. .................................................... 272/129
[58] Field of Search ......................................... 272/129

[56] References Cited

U.S. PATENT DOCUMENTS

| | | | |
|---|---|---|---|
| 4,544,154 | 10/1985 | Ariel | 272/129 |
| 4,628,910 | 12/1986 | Krukowski | 272/129 |
| 4,637,607 | 1/1987 | McArthur | 272/129 |
| 4,674,741 | 6/1987 | Pasierb, Jr. et al. | 272/129 |
| 4,678,184 | 7/1987 | Neiger et al. | 272/129 |
| 4,691,694 | 9/1987 | Boyd et al. | 272/129 |

Primary Examiner—Leo P. Picard
Attorney, Agent, or Firm—Darby & Darby

[57] ABSTRACT

A computer controlled exercise machine in which the user selects an exercise mode and its profile by programming the computer. Signals are produced by the program to control a resistive force producing device. Sensors produce data signals corresponding to the force applied to the actuating member of the system, velocity of movement and angular position which are continuously sampled at a high rate by a microprocessor operating under control of the program. The sampled data values are used to update and display performance results for the exercise and to compute the values of other parameters and, in some exercise modes, to control the amount of the resistive force.

19 Claims, 2 Drawing Sheets

COMPUTER CONTROLLED EXERCISE MACHINE

BACKGROUND OF THE INVENTION

Exercise machines for physical development and rehabilitation uses are well known and take a variety of forms. Typical forms include: user operated free weight machines, such as chest press, shoulder press, etc. on which weights are lifted along a straight line of either standard resistance or variable resistance form; cam operated machines to obtain a desired force curve; machines in which the user exercises against a pneumatic force, etc. Each such machine is designed to exercise one or more groups of muscles of an extremity or part of the body in a certain manner, i.e. to provide resistive force for the user to exercise against in a predetermined and position determined way. The force vs. position relationship is often called the force curve or force profile.

Typically, there are three modes of exercises that a user wishes to perform, these being the isometric, isotonic and isokinetic.

(a) In isometric mode exercises, the rate of angular change or velocity of the part of the body being exercised is zero, while the force can be applied in either of two directions. That is, the exercise is at zero velocity and only heat is developed as the user pushes or pulls against a non-movable object.

(b) In isotonic mode exercises, the load, or resistive force, has a constant value while the velocity varies. Such exercise mode is often performed on a standard resistance weight machine where weight plates are moved up and down a track as the user moves a lifting arm, foot pedal, etc.

(c) In isokinetic mode exercises, the force varies to match t user applied force in such a way that the velocity or force application is kept constant.

Each user desires to perform one or more exercise modes to satisfy different body development or rehabilitation goals. Each exercise would preferably have a force curve individualized for the user to match his goals and his strength capabilities. In the past, where machines using weight plates or friction type devices have been employed, this has required the use of several different types of machines and the mechanical adjustment of the resistive force. Such machines also have restriction in the number of modes and types of exercises that can be performed.

Attempts have also been made to select and control the exercise and its resistive force by the use of computers or microprocessors. See, for example, U.S. Pat. Nos. 4,354,676 to Ariel, 4,063,672 and 3,902,480 to Wilson and 3,869,121 to Flowell; and European Patent Application No. 83301887.2 (Publication 0095832A1). The devices disclosed in these patents and publications have various limitations both in the way in which the resistive force is produced and the variety and types of exercises that can be performed on them.

BRIEF SUMMARY OF THE PRESENT INVENTION

In accordance with the invention, a novel computer controlled exercise machine is provided wherein the user selects the exercise mode he wishes to perform and its parameters, such as force, velocity, etc. by programming them into the computer. The user then performs the exercise by way of moving an actuating member, for example, a rotatable member in either direction for up to or over 360°, which is coupled to a resistance producing device. In a preferred embodiment of the invention, the resistance producing device is of the electrically controlled type, such as a magnetic particle brake, which can produce the required amount of resistive force over a full 360° of rotation of the actuating member.

As the user moves the actuating member against the resistive force provided, the amount of force (torque) the user applies and its velocity (speed) is measured continuously and sampled on a continuous basis at high speed by the computer. These measured force application characteristics are used by the computer to calculate the results of the exercise parameters on a real time basis. They also can be compared against the characteristics of the force which is intended to be provided under the control of the program to achieve the desired exercise. Depending upon the exercise selected and its parameters, the computer produces appropriate control signals to adjust the resistance that the user encounters or monitors the force application.

The system of the invention is highly advantageous in that it is versatile and is able to accommodate a wide range of forces and velocities to be applied in a variety of exercise modes. It also has provisions to easily change both the selected mode and force curves on an individual basis to accommodate a wide range of users.

In addition, the results of the exercises performed by the user can be analyzed by the computer on a continuous basis to obtain information relating to items such as the force applied, velocity of application, angular position at which a predetermined, maximum or minimum amount of force or velocity is produced, exertion, etc. All of this information can be displayed concurrently with its production or recorded for use at a later time by the person exercising, a trainer or a therapist.

OBJECTS OF THE INVENTION

It is therefore an object of the present invention to provide a computer controlled exercise machine.

An additional object is to provide a computer controlled exercise machine for affording a variety of exercise modes to the user with the resistive force and velocity characteristics of the exercise either selected by the user or being pre-programmed.

A further object is to provide an exercise machine under computer control which continually monitors the efforts of the user.

Another object is to provide an exercise machine whose resistance producing mechanism is controlled by a computer in accordance with a selected program and in which the force the user applies to the machine and its velocity of application is monitored to produce control signals to adjust the machine's resistance producing mechanism to correspond to the selected programmed force characteristics.

BRIEF DESCRIPTION OF THE DRAWINGS

Other objects and advantages of the present invention will become more apparent upon reference to the following specification and annexed drawings in which.

DETAILED DESCRIPTION OF THE INVENTION

Figure 1:
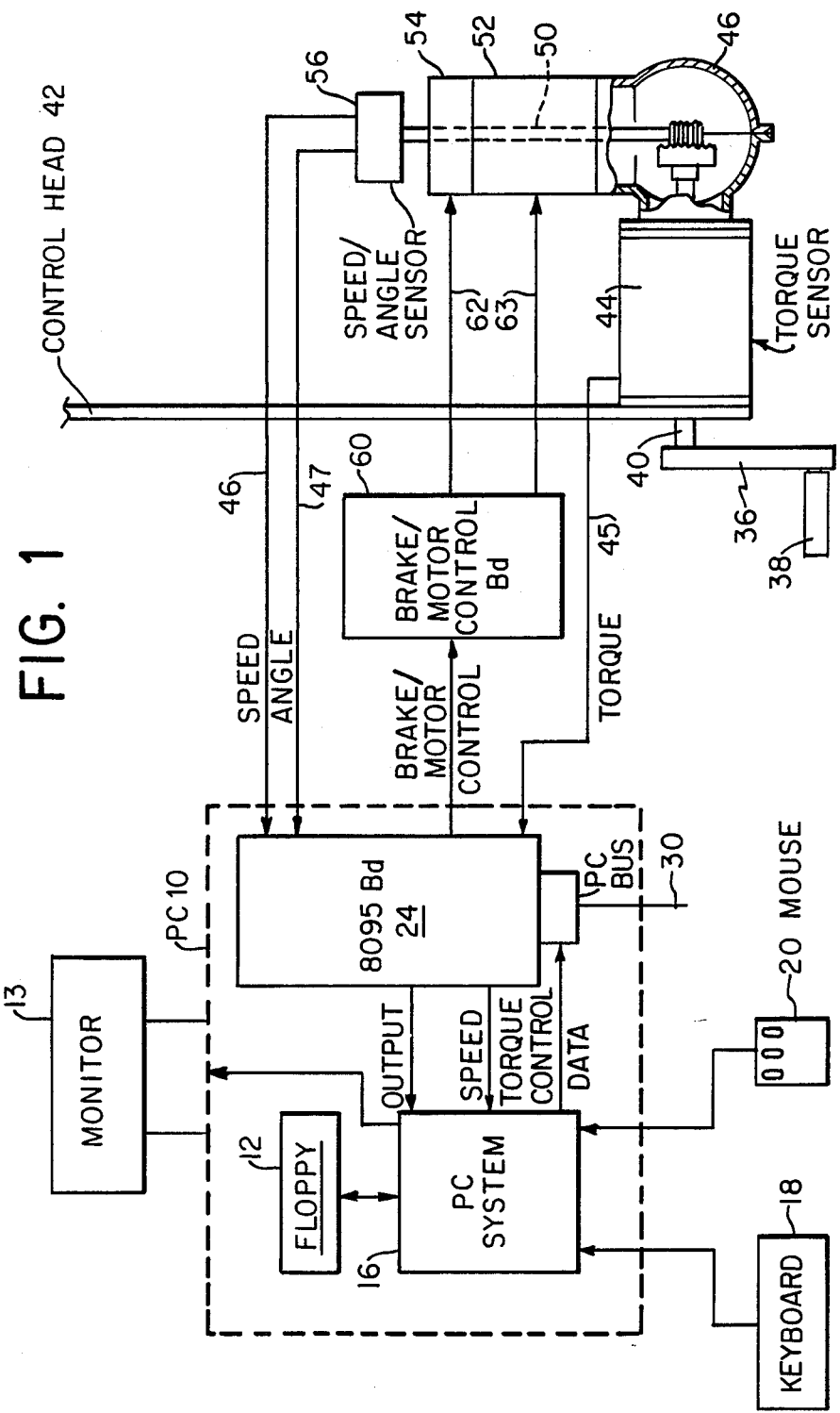
FIG. 1 is an overall block and schematic diagram of the system.

FIG. 1 is a schematic diagram of the system. It includes a computer 10, which is basically a high speed system which monitors torque, speed and shaft angle position data and outputs motor and brake control signals to effect the desired exercise type. It also formats and passes along torque and speed exercise results to a user interface computer having the usual microprocessor, ROM based instructions for utilities and peripherals, RAM memory keyboard, etc. The computer preferably includes a suitable replaceable storage device, for example, a conventional floppy disk device 12 which accepts disks having various programs stored thereon. The operating system for the computer and the parameters for the exercises for the individual users are stored on such discs. Results of the user's past performance in various exercises also can be stored on the disc.

The operating user interface portion of the computer is designated "PC" 16 to connote that it is of or comparable to the so-called personal microcomputer type. It has the necessary hardware and electronic circuits to interface with the peripheral input and output devices. In addition to the disc drive or drives 12, these include a keyboard 18 to enter numerical data such as the exercise parameters, respond to program commands, etc., a monitor 13 to display both input and output data, and preferably a "mouse" 20 which is used to move the cursor or icons on the display and to select an exercise. Such peripheral devices and their functions are also well known in the art.

The computer has the usual microprocessor board designated 24. Such board contains components such as the microprocessor itself, a ROM chip which has the instruction code to control the microprocessor and its arithmetic logic unit to perform various functions in accordance with the instructions which are supplied to the microprocessor from the program on the floppy disk, etc. All such components and functions are well known in the art.

A control data bus 30 on the board 24 receives control and data signals from the program inserted into the floppy disk 12 and the keyboard 18 or mouse 20. These signals are used to control the operation of and provide data to the microprocessor 24. The microprocessor 24 also receives data signals of the characteristics, i.e. quantity and velocity, of the force applied by the user.

Signals of the measured torque are produced on line 45, speed on line 46, instantaneous angle of the position of a shaft 40 during its rotation on line 47. If these signals are in analog form, the microprocessor board has suitable circuits to make an analog to digital (A/D) conversion. The direction of the shaft rotation can be computed either from the measured torque or angle signals. For example, a shaft angular position sensor will produce signals going in opposite directions, usually voltage changes is opposite polarity, for the two different directions of rotation.

In the operation of the system, the user inserts a control program disc into the disc drive 12. The disc has stored thereon one or more programs with data corresponding to desired exercise and its parameters. These can be either of the isometric, isotonic or isokinetic type. A variety of programs are preferably available on a single disc and are displayed when the exercise directory is called on the monitor 13. The user selects the particular exercise (mode) by the mouse 20 and its protocol (parameters) by operating the keyboard 18. That is, a single disc can contain programs corresponding to several different exercise modes and various strength level exercises in these modes. The user selects the exercise and then inserts the parameters, such as resistive force and velocity, on the points of inquiry such as certain angular positions of the shaft at which data is to be acquired, via the mouse and keyboard. There also can be exercise programs on the disc whose parameters cannot be modified.

As described in greater detail below in the preferred embodiment of the invention, the user applies force to a rotary actuator member. The torque and velocity of the applied force against the system provided resistive force are measured. The computer controlled exercise system of the present invention also has application where the force is applied linearly, along a curved path, etc. However, it has been found that the use of a rotational force through a full 360° gives greater versatility to the machine.

The part of the system which is mechanical and which the user confronts is generally shown on the right hand side of the drawing of FIG. 1. This includes a rotatable actuating member 36 which can have a rotatable handle 38 on its end. The actuating member 36 can be either a bar, wheel, etc. Member 36 has an output shaft 40 which extends through a control head panel 42 which is fixed, for example to the frame of the machine, relative to the shaft 40. The shaft 40 extends through a torque sensing device. A torque sensing collar, such as described in co-pending application Ser. No. filed 005037 filed 1/20/87 now U.S. Pat. No. 4,785,674 and assigned to the same assignee, is preferably used. Such device basically has one end fixed to frame 42 and the other end to a part, such as a gear box, movable in response to the applied force. The amount of "twist" of the collar between its two ends, which corresponds to the force applied by the user against the resistive force, is measured by a strain gauge, or other device, and its associated electronic circuitry. Any other suitable torque measuring device can be used, so the torque sensing device 44 is shown merely in block form.

The shaft 40 extends into a force reduction device. In a preferred embodiment, this is gear box 46 which is preferably a worm gear driven in the reverse manner. That is, the input drive gear at the end of the shaft 40 is larger than the output gear of the gear box 46. The gear box 46 itself has an output shaft 50 which actually is one end of the shaft of an electric motor 52 which has the usual stator (not shown) associated with its housing and the rotor (not shown) which would be located on the shaft 50. Motor 52 is preferably a high speed motor, for example, of the type in which high strength permanent magnets are on the rotor. The other end of shaft 50 extends into a brake 54 which is preferably a magnetic particle brake of the type such that variable resistance can be supplied in accordance with an electrical control signal supplied to the brake. A part of the shaft 50 extends through the brake and is coupled to a speed and angle position sensor 56, which can be of any conventional optical or mechanical type.

The disc to be inserted into the computer disc drive also contains the application or operating program. That is, this program instructs the computer on the rate of sampling of and how to use the measured torque, velocity, rotational direction and angular position data. Such instructions would instruct the microprocessor on what data is to be processed and how it is to be processed, the results to be calculated, the display of certain selected results and data, etc. It should be understood that some or all of the application program can be in a programmable read only memory (PROM or EPROM) which would be part of the computer system filmware/hardware instead of being part of the software on the disc. Such choice of techniques is well known.

After the exercise protocol is established, the information contained on the floppy disc in digital form is applied to the microprocessor board 24 in accordance with well known techniques. That is, it can be loaded into RAM on the circuit board or on the microprocessor all at once, in sequence, etc. Again, this is in accordance with the capacity of the computer and the manner in which the program on the disc is written. There also can be exercises on the disc whose parameters cannot be modified or selected by the user through the keyboard or mouse. The disc also can have the past results of prior performance by the user so that exercise results can be comparable and analyzed at different times. In a typical case, a history of one user can be kept on a disc, i.e. each user would have his own disc. If desired, this can be accomplished in a separate data disc.

The information supplied from the program is processed through the microprocessor 24 to initially send signals to a brake and motor controller circuit 60. This has the necessary circuitry to supply signals over a line 62 to control the magnetic particle brake 54 thereby to provide the desired amount of resistive force. Circuit 60 also provides a signal on line 63 to control the motor 52 which provides assistance to the user. That is, if a high speed, low resistive force (low torque), exercise is called for, a certain amount of inertia within the system such as from the gear box and the hysteresis value of the brake, must be overcome. To do this, signals are applied from circuit 60 to the motor 52 so that the motor provides an aiding force by rotating shaft 50 in the same direction that that the user turns it as he rotates input shaft 40.

As the user rotates the shaft 40, the torque is measured by the torque sensing device 44 and its associated electronic circuits. This measured torque is applied over line 45 to the microprocessor 24. Similarly, the measured speed of rotation and angular position information of shaft 40 is also supplied to the microprocessor 24. These measured parameters of torque, speed and angle can be processed by the microprocessor to compute and produce a display of a variety of quantities, e.g. instantaneous torque, speed, and power; average torque, speed and power; angular position of shaft for peak speed or peak torque; total and average exertion, etc. All of these measurements are made and processed on a high speed basis in accordance with he operation of the computer program. That is, the program instructs the microprocessor to use the measured information continuously to perform a variety of functions and computations at a rate of several hundred thousand times a second. Effectively, the continuously produced torque, speed and angle several hundred thousand times a second.

In at least the isokinetic mode of exercise, a comparison is made between the resistive force produced by the brake and a selected rotational velocity, as set by the program loaded into the computer through the floppy disc, and the amount of force actually being produced by the user as he rotates the shaft 40. It should be understood that this comparison is being done on a continuous high-speed basis in digital form. As a result of this comparison, the microprocessor board produces a control signal which is applied back to the brake/motor controller board to control the amount of resistive force presented to the user by brake 54 as he rotates shaft 40.

Figure 2:
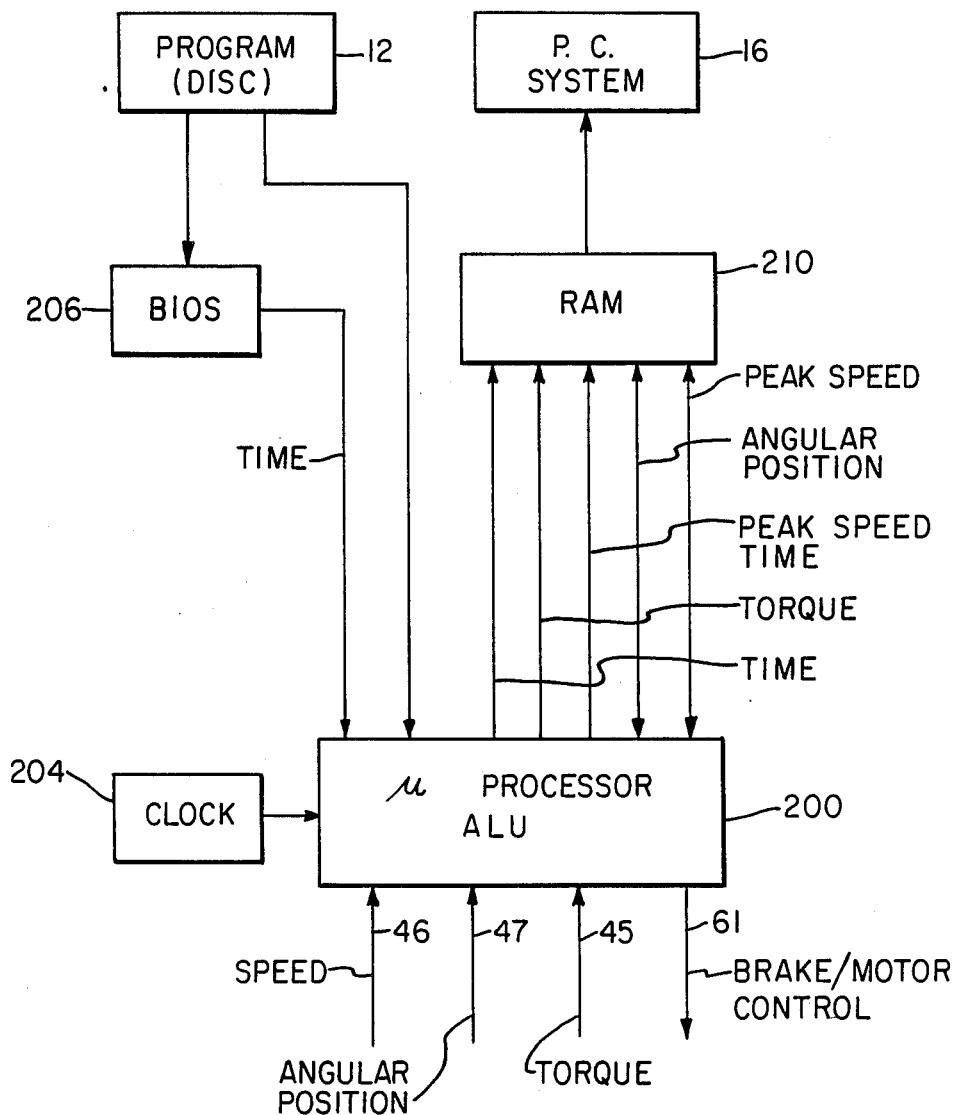
FIG. 2 is a schematic diagram showing how certain signals are compared and produced.

The operation of the system for its various exercise modes is now described. Reference is first made to FIG. 2 which is a block diagram illustrating the use of certain signals by the computer.

The microprocessor arithmetic logic unit (ALU) receives timing signals from a high frequency clock 204 which is part of the computer. It should be understood that all modern microprocessor units have a highly stable clock crystal which produces clock pulses at a rate of at least 4 Mhz and some as high as 16 Mhz or higher. Thus, it is a relatively simple matter and is conventional, to perform functions such as data sampling at a certain rate and at precise time intervals. The operating speed of the computer is made as high as possible, consistent with cost limitations. The microprocessor ALU also receives on lines 45, 46, 47 the digital version of the measured torque velocity and angular position signals previously described. From at least one of the latter two, the direction of shaft rotation is determined.

Microprocessor 24 also receives data from the program read out from the disc and operating instructions from the computer system BIOS 206 in accordance with instructions read from the program. These instructions control the operation of the ALU to perform its functions, e.g. add, subtract, compare, on the data applied to its own internal storage registers or at other memory locations, for example in a separate RAM 210, which is part of the PC system 16 to which the microprocessor has access.

The microprocessor ALU communicates with RAM 210 which stores the data of the various measurements and the results of calculations. The RAM in turn communicates through the PC system with one or more output devices such as the monitor 12, a printer, the disc drive 12 (to store its results) etc. All of the foregoing is conventional in the computer art.

ISOTONIC

The various exercise modes and some of the possible measured and computed results are now discussed.

In performing an isotonic exercise, the computer performs a number of functions. These are described below, using the prefix T (iso$\overline{\text{T}}$onic).

T1. Measurement of the peak speed (velocity)

That is, the signal produced by the speed sensor 56 is measured. A part of the computer RAM 210 is assigned to hold this speed data which is applied to it via the microprocessor. The computer program on the floppy disc instructs the microprocessor ALU to update this stored information at given times, which are measured in accordance with the signals supplied by the clock 204 and to replace the peak speed data stored in RAM when a new peak speed has been attained by the user. Effectively, the data of each new measured speed value is compared with the peak speed value previously stored and the new speed value is stored as the peak speed if it is greater than the stored value against which it is being compared. This value can be continuously displayed on an updated basis, or displayed and stored at given time intervals, or after the exercise cycle is completed in accordance with the control program on the disc or as a user selected option or both.

T2. Measurement of the angular position at which the peak speed occurs

It is sometimes desired to know at what angular position of rotation of the actuating member that the peak speed occurs. This is desired in situations where the machine is to be used for purposes of rehabilitation. This can be related, for example, to the responsiveness of a muscle group of an arm or leg at a predetermined position. This could be either during the extension of the arm or leg or its retraction. A therapist would keep a record of this over the times the user exercised to analyze the improvement or deterioration of the user's muscle group under consideration or the user himself would use it to monitor his progress toward his physical development goals.

The microprocessor ALU uses a part of the computer RAM 210 to store the angular position data which is continually produced by the sensor 56. Here, in the computer, each time the peak speed data is updated as described in T1, the angular shaft position (degree) data is also updated and stored in RAM. This is done under the system control program on the disc.

T3. Time to reach peak speed

This is related to the information developed in T1 above. When the user begins to exercise by turning the application member 36, the clock signals from clock 204 start to be counted to time the exercise cycle. The clock timing cycle is started, for example, upon a change in the angular position signal on line 47, or the torque and speed signals on lines 45 and 46 coming off a zero value. Here, also a part of the RAM 210 is assigned to hold the time data. Each time the peak speed data is updated, the time, starting from zero, at which the peak speed update occurs is also updated.

T4. Time to An isotonic exercise is at a constant (force) torque

This constant torque value is set as part of the control program, which can include an option for the user to set the value from the keyboard, and the signal needed to provide the required resistive force is applied to the brake control circuit to control the braking device 54. It will take the user some finite time to achieve this torque since it cannot be reached instantaneously. This information is also useful to the therapist or user in evaluating the condition and/or goals of the user. Here also, a part of the RAM 210 stores this data under the control of the ALU. The microprocessor ALU is operated by the control program to produce and store this time, starting from time zero of the exercise cycle, by comparing the torque set by the program or the user against the actual measured torque. When the former quantity is reached by the user rotating the shaft, the measured time is stored in RAM.

T5. Speed at a certain angular position

This is measured for a reason similar to the measurement of the angular position at which the peak speed occurs. That is, to evaluate a muscle group, which corresponds to a certain rotational position of the actuating member 36 as rotated by the user, the speed at that angular position is measured. This is done by the microprocessor ALU which is receiving data continuously on the speed and angular position of the shaft 50. At the angular position set by the control program, the speed is stored in computer RAM 210. If desired, the program is provided with the capability of measuring the speed at two or more angular positions of the shaft. The one or more angular positions are preferably selectable by the user, that is, they are variables selected by the user through the keyboard.

T6. Total work

This a measurement of the force extended (torque applied against the resistive force) by the user over the entire time he is exercising. In a rotational system where torque is applied, work (W) is measured as:

$$W = \int_{\theta 1}^{\theta 2} T d\theta$$

where
T = the torque applied in lb-ft = F (force applied) x
l = (length of moment arm)
$\theta$ = the total angular rotation of the shaft in degrees Starting from the beginning of the exercise cycle, the microprocessor ALU samples the measured torque data, which is produced continuously, at a fixed rate of several hundred thousand times per second and keeps track of the angular rotation of shaft 50. This data is stored in RAM on an additive basis. The stored value is converted into the desired units to be displayed, i.e. total foot pounds.

The total work value is being incremented continually in RAM so that the total work up to the given instant of each shaft angular position data update is available. This continuously incremented data is displayed at reasonable increments, e.g. once per second or half second, so that a display can be visualized and/be meaningful.

T7. Average Work

This value is developed on the basis of T6. That is, the total work value is not a linear time function since the user applied torque varies over time. The data on total work is always stored in RAM and is being continuously updated. To compute average work, the ALU measures the time since the start of the exercise cycle and it divides the total work by the elapsed time since the start of the exercise to compute the average work. This computed data is stored in RAM.

T8. Other data

With the data above described computed, other data also can be computed. For example:

a. average power—power is the rate of doing work. In T7, the average work is measured. Thus, the average power can be computed from this value.

b. average speed—this is the speed values measured at each increment which are averaged over the entire period of the exercise cycle. The average can be updated at each measurement increment.

c. exertion—there is an arbitrary quantity which can be used, if desired, to relate all three exercise modes. It is a measure of the force applied (torque) over a period of time, usually the time of the exercise cycle. That is, the torque data in lb-ft, as measured by 44, is stored in RAM 210 and its value incremented, i.e. so that there is a running sum of the torque. The time duration of the exercise cycle is also incremented and stored. Thus, there is a running product of torque times time, which is arbitrarily called "torque seconds". This value can be displayed and/or recorded on a running or final basis. The average exertion also can be computed for display or storage.

T. Bi-directional

The user can perform most exercises in two directions. That is, he can rotate the actuating member either clockwise or counter-clockwise. This corresponds to an extension or retraction of the muscle group being exercised. All of the foregoing results can be calculated for movement of the actuating member in either direction. The data for the results of the exercise in each direction is stored in memory and can be displayed or recorded. There would be two register locations for each measured and calculated parameter, one for each direction of rotation. In a typical case, the results will be compared on a one-for-one basis, that is, peak speed in both directions; angular position for peak speed in both directions, time to peak speed in both directions, etc.

T. Graphics—Graphic Display

It is often desirable that the user or person monitoring the exercise view the results. All of the foregoing measured and calculated results are available for display and can be displayed on a suitable visual display such as a video monitor. The results can be updated as the updates occur in computer memory or on a periodic basis such as once each ½ second or second, so that the display will be readable.

An overall isotonic graph can be presented for viewing. The graph preferably has, for example, the speed in degrees (of actuator member rotation) per second as the ordinate and the angular position of the actuating member as the abscissa. The latter can be dimensioned in any desired units, e.g. 10 degrees per unit. All of this information is available in computer memory on a real time basis and it can be displayed. In the isotonic mode exercise, it is sometimes desirable for the user to exercise and exert a small torque at a maximum speed. If the torque value is lower than the inertial losses of the mechanical parts of the system, i.e. the use cannot exert enough force to get the actuator member and connected shaft to rotating, the computer control program causes an assist signal to be produced which is applied via the motor/brake controller to the motor. The motor will turn in the same direction as the user is attempting to rotate the shaft.

ISOKINETIC

In the isokinetic mode, the computer program sets a constant velocity and the resistive force of brake 54 is varied as the user rotates the shaft so that this constant velocity is maintained. For example, if the user reduces the force he is applying, the computer will reduce the resistive force produced by the brake 54 so that the rotational speed will be kept constant.

Isokinetic exercises which are performed by the computer are described below using the prefix letter K (iso$\underline{K}$inetic). Where the measured functions are the same as ones previously described, they are so noted.

K1. Peak torque,

Here the continuously measured torque is respectively sampled at high speed as previously described. Each measurement is compared with a prior value of maximum torque stored in the RAM and if it exceeds such value, it is stored as the new peak torque value. That is, there is a register for torque value which is continuously compared and updated when a higher, peak torque value occurs.

K2. Angular position at which peak torque occurs

When the RAM is updated with a new peak torque value, the angular position as measured by the angular position sensor 54 at which said update occurs is also stored in RAM. This is done under the direction of the control program.

K3. Time to reach peak torque

As the exercise cycle starts, the timing of the cycle begins from zero. At each update of a peak torque value (K1), the time at which it occurs is stored K4. Time to Speed This is the time measured from the start of the exercise cycle to reach the velocity set in by the computer program. Such velocity value also can be selected by the user via the keyboard. That is, the measured speed data is compared against the set speed and when the former equals the latter, the time at which this occurs is stored.

K5. Maximum Speed

In some cases, the user will not reach or will exceed the speed set by the program. The speed measured at each sampling time is stored and the RAM is updated each time a value higher than the stored value is measured. That is, the highest speed that the user reaches is stored in RAM. This value may be less than the value set i for exercise.

K6. Torque at Certain Angular Position

When exercising a certain part of the body, it may be desired to determine what was the torque at a certain position of the body limb. Accordingly, the program can set in one or more angular positions (degrees) and store the measured torque value at such angular position(s). In the ALU the torque measured at the selected angular position is sampled and updated into the RAM.

K7. Total Work. See T6.

K8. Average Work. See T7.

K9. Average Power. See T8a.

K10. Exertion. See T8c

The use of this quantity permits a quantitative estimate, or a "figure of merit" to be made among the various exercise modes. It should be understood that the isotonic and isokinetic modes require motion of the actuating member when the isometric mode does not require motion.

K. Bidirectional. See T Bidirectional

As discussed, any of the measurements and calculations can be made with the actuating member turning in either direction K. Graphics—See T Graphics As discussed, any of the measured or computed data can be displayed.

overall isokinetic graph can be presented for viewing as the user performs the exercise. This graph preferably displays the instantaneous work being performed, in foot pounds, as the ordinate and the angular position of the shaft (in degrees) as the abscissa. As before, the latter can be in any desired units, e.g. 10 degrees, of angular rotation.

ISOMETRIC

In an isometric (iso$\underline{M}$etric) mode exercise, the rate of angular change of velocity of the part of the body being exercised is zero, i.e. the velocity or speed is constant, and the exercise can be in either of two directions. That is, the user attempts to rotate the actuating member in either direction against the resistive force of the brake. An isometric exercise involves the muscular exertion of force against a stationary load and allows for the maximum effort of a specific number of muscle fibers dedicated to a muscle joint angle. Since no motion occurs, the only by-product of this type of muscle exertion is heat. That is, the user exercises against the load and a measurement is to be made of his exerted force. The load set in by the computer to the brake 54 must be large enough so that it cannot be overcome. Also the angular position of the actuating member at which the exercise is performed can be selected.

The various measurements made and results calculated in this exercise are discussed below.

M1—Peak Torque

This is a measurement of the peak force applied by the user. It should be understood that to produce a torque force required so movement since torque is the product of force time a moment arm (the length of the actuator member). During each measured data sample, the amount of torque measured is compared with the peak torque stored and if the current measured torque value is greater than the stored value, an update is made of the new peak value.

M2—Degree at Peak explained previously, here the angular degree at which the peak torque occurs is stored. This is also updated as the peak torque value is updated.

M3—Torque at Specific Angular Position(s)

As described before (K6), it is sometimes desired to measure the torque applied at a specific angular position in opposition to the constant load. This can be done since the angular position of the actuating member is always known. A value of the angular position, or several such positions, set into the program, will cause the ALU to store into the RAM the torque at such position(s).

As previously described, other calculations can also be made in a similar manner, these being total work, average work, total exertion, average exertion, etc. In addition, the measurements are made and the results calculated for both directions of force exertion against the actuating member.

As before, all of the measured values and calculated results can be displayed and/or recorded as desired. For a display of the overall isometric exercise graph, the ordinate would be the torque applied (in lb-ft) and the abscissa would be the time of application, in selected units, e.g. ½ second.

Individual Dynamic Variable Resistance Mode

Another form of exercise is a variable resistance which has worked, for example, in a chest press, of mechanical construction, and arrangement is provided for varying the resistance upon an extension of the limb being exercised.

The present machine has the capability for also performing a variable resistance excerise mode tailored to an individual user. In a variable resistance mode, the user is to exercise against a force which varies depending upon the position of extension or retraction of the limb which is being exercised. For example, when exercising an arm, the user has more power when the arm is fully extended. Thus, it is desirable to tailor the amount of resistance that the user exercises against during rotation of the actuating member.

To do this, the user uses the computer in a record mode and then rotates the actuating member. In so doing, the torque that the user exerts at its position of extension or retraction of the limb is recorded. This record is then used to set the user's own individual dynamic variable resistance (IDVR) force curve.

When the user is ready to exercise, he selects the IDVR made and his force curve and begins to exercise. He can vary the magnitude of the force curve. During such exercise over the range of movement of the actuating member, various parameters can be measured as explained before in connection with the exercise modes discussed above. This can be, for example, peak speed, degree at which peak speed occurs, time to peak speed, total work, average work, average power, total exertion, etc.

In addition, a graphical display can be presented of the speed at which the user is rotating the actuator member (in degrees per second) as the ordinate and the angular position of the shaft in degrees.

The system has been described with respect to the user performing "passive" exercises. That is, the user exercises and moves the actuating member against an existing force, and the actuating member is otherwise stationary. The system also can be used in "active" mode exercises. In such exercise, the system turns the actuating member and the user exerts force to prevent the turning so as to keep the actuating member stationary. This can be accomplished by suitably controlling the motor 52 to turn the shaft 50 with the desired amount of torque so that the user can apply force against this.

As mentioned previously, the system can be used with actuating members which move in a direction other than rotational, e.g. linear.

What is claimed is:

1. An exercise system for performing a variety of exercises comprising:
   computer means,
   means for producing a relative force,
   means operated by said computer means for controlling the amount of resistive force produced by said force producing means,
   an actuating member for operation by the user against such resistive force,
   means operated by said computer means for initially driving said actuating member in a direction so as to aid the user to overcome said force,
   means for measuring the force applied to said actuating member, and for producing signals corresponding thereto,
   said computer means sampling the data values of said signals on a high speed basis.

2. A system as in claim 1 wherein said actuating means is movable and said measuring means also measures the velocity of motion of said actuating member in response to the applied force.

3. A system as in claim 1 wherein said actuating member is rotational and is to be rotated by the user and the measured forced is the applied torque.

4. A system as in claim 3 wherein said actuating means is movable and said measuring means also measures the velocity of motion of said actuating member in response to the applied force.

5. A system in claim 4 wherein said measuring means measures the torque applied to said actuating means and the speed of its rotation.

6. A system as in claim 5 wherein said measuring means also measures the angular position of said rotatable actuating member.

7. A system as in claim 3 further comprising means for calculating the torque applied by the user over at least a part of the time of an excerise cycle.

8. A system as in claim 1 further comprising:
   means for supplying information to said computer corresponding to an excerise to be performed;
   and means responsive to said information for controlling said resistive force producing means.

9. A system as in claim 8 wherein said actuating member is rotational and is to be rotated by the user and the measured force is the applied torque.

10. A system as in claim 9 wherein said actuating means is movable and said measuring means also measures the velocity of motion of said actuating member in response to the applied force.

11. A system as in claim 10 wherein said measuring means measures the torque applied to said actuating means and the speed of its rotation.

12. A system as in claim 1 further comprising means controlled by said computer providing a force to said actuating member to and the force applied by said user.

13. A system as in claim 12 further comprising means for supplying information to said computer corresponding to an exercise to be performed;

and means responsive to said information for controlling said resistive force producing means.

14. A system as in claim 1 wherein said actuating member is movable, and further comprising said computer means having means to record a force curve applied by the user to said actuating means as it moves, and means for controlling said resistance producing means in accordance with the recorded force curve of the user.

15. An exercise system operated by a user for performing a variety of exercise comprising:
   computer means,
   means for producing a resistive force,
   means operated by said computer means for controlling the amount of resistive force produced by said force producing means,
   an actuating member for operation by the user against such resistive force,
   means for measuring the force applied to said actuating member, and for producing signals corresponding thereto,
   said computer means sampling the data values of said signals on a high speed basis,
   means for operating said computer means in a recording mode to record data corresponding to the variable force exerted by a user against said actuating means during the performance of an excerise movement, as measured by said measuring means, to produce recorded data thereof, and
   means for operating said computer in an exercise mode subsequent to said recording mode to cause said means for controlling to control the amount of resistive force produced by said force controlling means in relationship to said recorded data.

16. A system as in claim 15 further comprising means for varying the recorded data to be used by the computer to operate said means for controlling the relative force produced.

17. A method for producing an individualized variable resistance excerise for a user comprising the steps of:
   having the user exercise against an actuating member,
   measured the variable amount of force applied by said user against said actuating member as the user performs an excerise movement,
   recording as a data signal the variable amount of force measured in said measuring step,
   providing a controllable resistive force producing means operable to resist the movement of said actuating member,
   after said recording step, having the user excerise by moving said actuating member against the resistive force produced by said controllable resistive force producing means operated so as to resist the movement of said actuating member, and
   during the user's exercise, controlling the amount of force produced by said controllable resistive force producing means in relationship to said recorded data.

18. A method as in claim 17 wherein said step of controlling said controllable resistive force producing means in response to said recorded data is accomplished by a computer.

19. A method as in claim 17 further comprising the step of varying the recorded data signal before it is used to control the amount of resistive force produced by said controllable resistive force producing means.

* * * * *

UNITED STATES PATENT AND TRADEMARK OFFICE
CERTIFICATE OF CORRECTION

PATENT NO. : 4,869,497

DATED : September 26, 1989

INVENTOR(S) : Gary D. Sterart et al

It is certified that error appears in the above-identified patent and that said Letters Patent is hereby corrected as shown below:

On the title page the following name should be added as an inventor in item [75]:

--John K. Geist--

Signed and Sealed this

Tenth Day of July, 1990

*Attest:*

HARRY F. MANBECK, JR.

*Attesting Officer*      *Commissioner of Patents and Trademarks*